United States Patent
Gedulin et al.

(10) Patent No.: US 8,168,233 B2
(45) Date of Patent: May 1, 2012

(54) TREATMENT OF PANCREATITIS WITH AMYLIN

(75) Inventors: Bronislava Gedulin, Del Mar, CA (US); Andrew A. Young, La Jolla, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 929 days.

(21) Appl. No.: 10/671,304

(22) Filed: Sep. 24, 2003

(65) Prior Publication Data

US 2005/0070472 A1    Mar. 31, 2005

Related U.S. Application Data

(60) Provisional application No. 60/419,440, filed on Oct. 18, 2002.

(51) Int. Cl.
*A61K 36/00* (2006.01)
(52) U.S. Cl. .................................. 424/725; 514/1.1
(58) Field of Classification Search .................. 514/12
See application file for complete search history.

(56) References Cited

U.S. PATENT DOCUMENTS

| | | | |
|---|---|---|---|
| 4,370,317 A * | 1/1983 | Jorgensen et al. | 514/12 |
| 5,124,314 A | 6/1992 | Cooper | |
| 5,196,402 A * | 3/1993 | Braganza et al. | 514/9 |
| 5,234,906 A | 8/1993 | Young et al. | |
| 5,264,372 A | 11/1993 | Beaumont et al. | |
| 5,436,169 A * | 7/1995 | Iovanna et al. | 436/518 |
| 5,516,651 A | 5/1996 | Goldring et al. | |
| 5,677,279 A * | 10/1997 | Young | 514/12 |
| 5,686,411 A | 11/1997 | Gaeta et al. | |
| 5,998,367 A | 12/1999 | Gaeta et al. | |
| 6,114,304 A | 9/2000 | Kolterman et al. | |
| 6,251,926 B1 | 6/2001 | Momose et al. | |
| 6,410,511 B2 | 6/2002 | L'Italien et al. | |
| 6,610,824 B2 | 8/2003 | Gaeta et al. | |
| 6,869,926 B1 * | 3/2005 | Reid et al. | 514/2 |
| 7,045,533 B2 * | 5/2006 | Brain et al. | 514/311 |
| 2001/0018049 A1 * | 8/2001 | Sachs et al. | 424/94.1 |
| 2003/0092606 A1 | 5/2003 | L'Italien et al. | |

FOREIGN PATENT DOCUMENTS

| EP | 0289287 | | 1/1998 |
|---|---|---|---|
| SU | 1979-66671 B | * | 9/1978 |
| WO | WO 93/10146 | | 5/1993 |

OTHER PUBLICATIONS

Haddad et al. (The use of a low fat diet in the treatment of acute pancreatitis, American Journal of Gastroenterlogy, (Sep. 2000), vol. 95, No. 9, pp. 2479).*
Brand et al., Int. J. Gastrointest Cancer (2002) 31(1-3): 123-128.
Clark et al., Diabetes Res Clin Pract. Aug. 28, 1995 Suppl.: S39-47.
Garg et al., Diabetes Care Jan. 19, 1996 (1): 28-31.
Gasiorowska et al., Hepatogastroenterology Jan.-Feb. 2003 50(49): 258-262.
Gedulin et al., Diabetes (1998) 47 (Suppl 1), abstract 1086.
Goebell et al., Scand J Gastroenterol (1979) 14: 881-889.
Goebell, Demeter Verleg (1976): 28-31.
Goebell, Excerpta Medica (1981), Int. Cong. Ser. 540, 346-351.
Hotz et al., Res Exp Med (Berl) 1973, 160 152-165.
Luisetto, Excerpta Medica (1981), Int. Cong. Ser. 540, 336-345.
Morley et al., Peptides (1991) 12:865-869.
Odes et al., S. Afr. Med J. (1978) 53, 201-203.
Paul, Dtsch Med Wochenschr (1979) 104, 615-622.
Phillips et al., Eur Surg Res (1999) 31(6): 457-464.
Phillips et al., Pancreas Jan. 2000 20(1):105-106.
Schmidt, Dtsch Med Wochenschr (1971), 96 1773-1775.
Young, A.A., et al. Diabetologia (1995) 38:642-648.
International Search Report dated Oct. 4, 2004 from International Application No. PCT/US03/30224 (1 page).
Cooper, et al, "Amylin Found in Amyloid Deposits in Human Type 2 Diabetes Mellitus . . . " Proc. Acad. Sci. USA (1988) 85 pp. 7763-7766.
Cooper, et al, "The Amylin Superfamily: A Novel Grouping of Biologically Active Polypeptides Related to the Insulin A-Chain" Prog Growth Factor Res. (1989) 1 pp. 99-105.
Gedulin, et al, "Dose-Response for Glucagonostatic Effect of Amylin in Rats" Metabolism (1997) 46:1 pp. 67-70.
Gedulin, et al, "Amylin Inhibits Pentagastrin-Stimulated Gastric Acid Secretion and Protects Against Ethanol-Induced . . . " Diabetologia (1997) 40:A299 (Abstract 1177).
Leighton, et al, "Pancreatic Amylin and Calcitonin Gene-Related Peptide Cause Resistance to Insulin in Skeletal Muscle in vitro" Nature (1988) 335:6191 pp. 632-635.
Munson, et al, "Ligand: A Versatile Computerized Approach for Characterization of Ligand-Binding Systems" Anal Biochem (1980) 107 pp. 220-239.
Ogawa, et al, "Amylin Secretion from the Rat Pancreas and its Selective Loss After Streptozotocin Treatment" J Clin Invest (1990) 85 pp. 973-976.
Silvestre, et al, "Inhibitory Effect of Rat Amylin on the Insulin Responses to Glucose and Arginine in the Perfused Rat Pancreas" Regul Pept (1990) 31 pp. 23-31.
Warzecha, et al, "Effect of Sensory Nerves and CGRP on the Development of Caerulein-Induced Pancreatitis and Pancreatic Recovery" J. Physio and Pharm (2001) 52:4 pp. 679-704.
Warzecha, et al, "The Influence of Sensory Nerves and CGRP on the Pancreatic Regeneration After Repeated Episodes of Acute . . . " J Physio and Pharma (2000) 51:3 pp. 449-461.

* cited by examiner

*Primary Examiner* — Christopher R Tate
*Assistant Examiner* — Randall Winston (57) ABSTRACT

The disclosed invention provides for the treatment of pancreatitis, and the alleviation of pain associated therewith, with amylin, amylin agonists and amylin analogs.

13 Claims, 2 Drawing Sheets

TREATMENT OF PANCREATITIS WITH AMYLIN

CROSS REFERENCE TO RELATED APPLICATIONS

This application claims the benefit of priority to U.S. Provisional Patent Application Ser. No. 60/419,440, filed Oct. 18, 2002, and incorporates in its entirety the contents thereof.

FIELD OF THE INVENTION

The invention relates to the treatment of pancreatitis by use of amylin and amylin analogs. The invention provides methods of treating both acute and chronic forms of pancreatitis, as well as the pain associated with the conditions. Also provided are methods for the use of agonists at receptors for amylin.

INCORPORATION OF SEQUENCE LISTING

A paper copy of the Sequence Listing and a computer readable form of the sequence listing on diskette, containing the file named 18528.643.SeqList.txt, which is 2,704 bytes in size (measured in MS-DOS), and which was created on Dec. 2, 2004, are herein incorporated by reference.

BACKGROUND OF THE INVENTION

The human pancreas secretes over a liter of enzyme and zymogen containing fluid per day as part of its role in the major digestive activity of the gastrointestinal tract. Regulation of pancreatic secretion is by both hormonal and neural mechanisms, with the former being of primary importance. The secreted enzymes include amylases, lipases, and proteolytic enzymes, which may be packaged in precursor form or in combination with inhibitors to prevent autodigestion of pancreatic cells. Enzyme secretion is also regulated in part by a negative feedback mechanism induced by enzyme levels in the duodenum.

Pancreatitis is an inflammatory disease which may be clinically diagnosed as acute or chronic. For a review of the above, see Greenberger N J et al. Chapter 260: Acute and Chronic Pancreatitis. Wilson J D et al. eds. Harrison's Principles of Internal Medicine. 12th Ed. New York: McGraw Hill, 1991: 1372-83. See also the web site of by eMedicine.com, Inc., emedicine.com/med/topic1720.htm, and The Merck Manual of Diagnosis and Therapy, section 3, chapter 26, an online version of which can be found on the merck.com website at merck.com/pubs/mmanual/section3/chapter26/26b.htm, for a full description of the pathophysiology, clinical course, and current treatment of acute and chronic pancreatitis.

If pancreatic enzymes and toxins released during acute pancreatitis gain access to the system circulation via retroperitoneal, lymphatic and/or venous pathways, they can affect capillaries and generally cause harmful systemic effects. Respiratory distress syndrome, renal failure and/or heart failure are the most frequent causes of death in patients with acute pancreatitis.

An estimated 50,000 to 80,000 cases of acute pancreatitis occur in the U.S. each year. Most cases in the U.S. are caused either by alcohol abuse or by gallstones. Other causes may be use of prescription drugs, trauma or surgery to the abdomen, or abnormalities of the pancreas or intestine. In rare cases, the disease may result from viral infections, such as mumps. In about 15% of cases, the cause is unknown.

Acute pancreatitis occurs suddenly and may be a severe, life-threatening illness with many complications. Usually, the condition is self-limited and the patient recovers completely. The major symptom is abdominal pain, and conventional treatments include analgesics for pain, intravenous fluids, no oral intake, and nasogastric suction to decrease gastrin release from the stomach.

If injury to the pancreas continues, such as when a subject persists in drinking alcohol, a chronic form of the disease may develop, bringing severe pain and reduced functioning of the pancreas that affects digestion and causes weight loss. Chronic pancreatitis may also result from other causes, many of which are also known to induce acute pancreatitis. Chronic pancreatitis may also develop from undetermined causes. While pain is also often seen in chronic pancreatitis, the pain may be continuous or intermittent or absent.

In contrast to acute or reoccurring acute pancreatitis, serum amylase and lipase levels are not elevated in patients with chronic pancreatitis. Oral administration of conventional pancreatic enzymes have been demonstrated to decrease abdominal pain in patients with chronic pancreatitis. This observation is consistent with the negative feedback regulation hypothesized for pancreatic exocrine secretion.

Generally, therapeutic approaches used to date against pancreatitis aim to minimize further enzyme secretion (limiting further damage and inflammation), treat pain (for which narcotics may be required), maintain circulatory function, prevent secondary infection, and eventually, in chronic cases, correction of malabsorption. Strategies for limiting enzyme secretion include:

1) preventing passage of nutrients from the stomach into the duodenum (such as by nasogastric suction and intravenous alimentation);
2) preventing acid from entering the duodenum (which normally prompts secretin release and results in pancreatic stimulation; it should be noted that cimetidine to limit acid secretion has not been shown useful in treating pancreatitis);
3) blocking enzymatic secretion, as with anticholinergic drugs for example (which has not been shown useful); and
4) inhibiting protease activity, as with aprotinin (Traysylol™) for example (which has been shown ineffective in practice).

Amylin, a 37 amino acid peptide hormone co-secreted with insulin in response to nutrient stimuli from pancreatic β-cells, inhibits insulin secretion from β-cells and glucagon secretion from α-cells (see Cooper, G. J., et al., *Prog. Growth Fact. Res.* (1998) 1:99-105, Ogawa et al. *J. Clin. Invest.* (1990) 85:973-976, Silvestre, R. A., et al., *Regul. Pept.* (1990) 31:23-31, Young, A. A., et al., *Diabetologia* (1995) 38:642-648, and Gedulin, B. R., et al., *Metabolism* (1997) 46(1):67-70). Amylin, at doses resulting in physiological plasma concentrations, regulates nutrient absorption by inhibiting gastric emptying, food intake and, in a rat model of cholecystokinin octapeptide (CCK-8), induces lipase and amylase secretion (see Young et al., Morley et al. *Peptides* (1991) 12:865-869, Gedulin et al. *Diabetes* (1998) 47(Suppl 1), abstract 1086). Amylin showed no effect on basal pancreatic enzyme secretion in the rat model. Additionally, it inhibits gastric acid secretion with similar potency (see Gedulin, B., et al., *Diabetologia* (1997) 40(Suppl 1), abstract 1177).

Amylin has been examined extensively in preclinical and clinical settings (e.g., as a treatment for diabetes), and is well tolerated by animals, including humans.

SUMMARY OF THE INVENTION

The present invention is directed to the use of amylin and amylin agonists, including analog agonists, to treat pancreatitis, and the symptoms associated therewith, in animals afflicted or diagnosed with pancreatitis. The invention may also be used to improve or otherwise supplement known methods of treating pancreatitis.

In one aspect, compositions and methods for the treatment of both acute and chronic mammalian or human pancreatitis with amylin are provided. The compositions and methods may also be used for the treatment of pain associated with pancreatitis.

In a further aspect, pancreatitis is treated with an agonist for a receptor activated by amylin. Such agonists may be small molecules or proteinaceous in nature and may include antibodies which activate a receptor for amylin.

In another aspect, a precursor or proform of amylin (e.g., a cleavable recombinant form, an analog thereof, or an agonist at a receptor activated by amylin may be used to treat pancreatitis. In yet another aspect of the invention, amylin, an analog or precursor thereof, or an agonist of an amylin receptor may be used in combination with an agent known to be effective in the treatment of pancreatitis and/or a pain relief agent known in the art. The amylin agonists, analogs and related compounds of the invention discussed herein may also be used in the prevention of pancreatitis.

The invention also provides for a pancreatic cell that has been contacted or treated with amylin, an analog or precursor thereof, or an agonist of an amylin receptor. Such a cell would be afflicted by pancreatitis and have the gene expression profile of a cell that is so afflicted.

DETAILED DESCRIPTION

The present invention is directed to the use of an amylin or an analog thereof to treat pancreatitis and the symptoms associated therewith. Preferred animals for the application of the present invention are mammals, particularly those important to agricultural applications (such as, but not limited to, cattle, sheep, horses, and other "farm animals") and for human companionship (such as, but not limited to, dogs and cats). Particularly preferred subjects in the treatment of pancreatitis are humans.

As used herein, the terms "treat," "treating," or "treatment" refer to alleviating (or lessening the severity) of any one or more molecular, biological, or clinical effects associated with the disease of pancreatitis, whether acute or chronic. For example, and without limiting the invention, the terms include reducing or inhibiting the level of inflammation, enzymatic activity or enzymatic secretion in pancreatic cells. In preferred embodiments of the invention, the terms include reducing the level of enzymatic secretion or activity below deleterious levels.

"Amylin" as used herein refers to compounds such as those described in U.S. Pat. No. 5,124,314, issued Jun. 23, 1992, and U.S. Pat. No. 5,234,906, issued Aug. 10, 1993, both of which are hereby incorporated by reference as if fully set forth. The term includes, but is not limited to, a human peptide hormone of 37 amino acids referred to as amylin, which is co-secreted with insulin from β-cells of the pancreas. Human amylin has the following amino acid sequence: Lys-Cys-Asn-Thr-Ala-Thr-Cys-Ala-Thr-Gln Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO:1). The term also includes variants of amylin as present in, and in isolatable form, other mammalian species. With respect to a naturally occurring amylin compound, the term includes such a compound in an isolated, purified, or other form that is otherwise not found in nature.

An "agonist" of amylin refers to a compound that mimics one or more effects (or activity) of amylin in vitro or in vivo. The effects of amylin include the ability to directly or indirectly interact or bind with one or more receptors that are activated or deactivated by amylin, for example, the receptor binding assay and the soleus muscle assay described in Examples 2 and 3, respectively. Preferably, the amylin agonist is not a calcitonin, which, as used herein, refers to the human peptide hormone calcitonin and species variations of it, such as that of rat, salmon and eel (including aminosuberic eel calcitonin).

An "analog" (or "analogue" or "agonist analog") of amylin refers to a compound that is similar in structure (e.g., derived from the primary amino acid sequence of amylin by substituting one or more natural or unnatural amino acids or peptidomimetics) to amylin and mimics an effect of amylin in vitro or in vivo. Amylin analogs useful in the invention may also include fragments of amylin such as those described in EP 289287, the contents of which are herein incorporated by reference. Preferred amylin agonists may also be compounds having at least 60, 65, 70, 75, 80, 85, 90, 95, or 99% amino acid sequence identity to SEQ ID NO: 1 and having amylin activity. Amylin analogs also include amylin having insertions, deletions, and/or substitutions in at least one or more amino acid positions of SEQ ID NO: 1. The number of amino acid insertions, deletions, or substitutions may be at least 5, 10, 15, 20, 25, or 30. Insertions or substitutions may be with other natural or unnatural amino acids, synthetic amino acids, peptidomimetics, or other chemical compounds.

Exemplary amylin agonist analogs contemplated in the use of the invention include those described in U.S. Pat. Nos. 5,686,411, 6,114,304, and 6,410,511, which are herein incorporated by reference in their entirety. Such compounds include those having the formula (SEQ ID NO: 2)
$^1A_1$-X-Asn-Thr-$^5$Ala-Thr-Y-Ala-Thr-$^{10}$Gln-Arg-Leu-$B_1$-

Asn-$^{15}$Phe-Leu-$C_1$-$D_1$-$E_1$-$^{20}F_1$-$G_1$-Asn-$H_1$-Gly-$^{25}I_1$-$J_1$-

Leu-$K_1$-$L_1$-$^{30}$Thr-$M_1$-Val-Gly-Ser-$^{35}$Asn-Thr-Tyr-Z wherein $A_1$ is Lys, Ala, Ser or hydrogen;
$B_1$ is Ala, Ser or Thr;
$C_1$ is Val, Leu or Ile;
$D_1$ is His or Arg;
$E_1$ is Ser or Thr;
$F_1$ is Ser, Thr, Gln or Asn;
$G_1$ is Asn, Gln or His;
$H_1$ is Phe, Leu or Tyr;
$I_1$ is Ala or Pro;
$J_1$ is Ile, Val, Ala or Leu;
$K_1$ is Ser, Pro, Leu, Ile or Thr;
$L_1$ is Ser, Pro or Thr;
$M_1$ is Asn, Asp, or Gln;
X and Y are independently selected amino acid residues having side chains which are chemically bonded to each other to form an intramolecular linkage; and Z is amino, alkylamino, dialkylamino, cycloalkylamino, arylamino, aralkylamino, alkyloxy, aryloxy or aralkyloxy; and provided that when (a) $A_1$ is Lys, $B_1$ is Ala, $C_1$ is Val, $D_1$ is His, $E_1$ is Ser, $F_1$ is Ser, $G_1$ is Asn, $H_1$ is Phe, $I_1$ is Ala, $J_1$ is Ile, $K_1$ is Ser, $L_1$ is Ser, and $M_1$ is Asn;

(b) $A_1$ is Lys, $B_1$ is Ala, $C_1$ is Ile, $D_1$ is Arg, $E_1$ is Ser, $F_1$ is Ser, $G_1$ is Asn, $H_1$ is Leu, $I_1$ is Ala, $J_1$ is Ile, $K_1$ is Ser, $L_1$ is Pro, and $M_1$ is Asn;

(c) $A_1$ is Lys, $B_1$ is Ala, $C_1$ is Val, $D_1$ is Arg, $E_1$ is Thr, $F_1$ is Ser, $G_1$ is Asn, $H_1$ is Leu, $I_1$ is Ala, $J_1$ is Ile, $K_1$ is Ser, $L_1$ is Pro, and $M_1$ is Asn;

(d) $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Pro, $J_1$ is Val, $K_1$ is Pro, $L_1$ is Pro, and $M_1$ is Asn;

(e) $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Pro, $J_1$ is Val, $K_1$ is Ser, $L_1$ is Pro, and $M_1$ is Asn; or (f) $A_1$ is Lys, $B_1$ is Thr, $C_1$ is Val, $D_1$ is Arg, $E_1$ is Ser, $F_1$ is Ser, $G_1$ is His, $H_1$ is Leu, $I_1$ is Ala, $J_1$ is Ala, $K_1$ is Leu, $L_1$ is Pro, and $M_1$ is Asp; then one or more of $A_1$ to $M_1$ is a D-amino acid and Z is not amino.

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

An additional aspect of the present invention is directed to agonist analogues of SEQ ID NO:2 which are not bridged, and wherein X and Y are independently selected from Ala, Ser, Cys, Val, Leu and Ile or alkyl, aryl, or aralkyl esters and ethers of Ser or Cys.

Biologically active derivatives of the above agonist analogues are also included within the scope of this invention in which the stereochemistry of individual amino acids may be inverted from (L)/S to (D)/R at one or more specific sites.

Also included within the scope of this invention are the agonist analogs modified by glycosylation of Asn, Ser and/or Thr residues.

Biologically active agonist analogs of amylin are included within the scope of this invention which contain less peptide character. Such peptide mimetics may include, for example, one or more of the following substitutions for —CO—NH— amide bonds: depsipeptides (—CO—O—), iminomethylenes (—CH$_2$—NH—), trans-alkenes (—CH=CH—), beta-enaminonitriles (—C(=CH—CN)—NH—), thioamides (—CS—NH—), thiomethylenes (—S—CH$_2$— or —CH$_2$—S—), methylenes (—CH$_2$—C$_2$—) and retro-amides (—NH—CO—).

Compounds of this invention form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkaline earth salts (such as calcium and magnesium salts). Acetate, hydrochloride, and trifluoroacetate salts are preferred.

Exemplary compounds include, but are not limited to des-$^1$Lys-h-amylin, $^{28}$Pro-h-amylin, $^{25,28,29}$Pro-h-amylin, $^{18}$Arg$^{25,28}$Pro-h-amylin, and des-$^1$Lys$^{18}$Arg$^{25,28}$Pro-h-amylin, all show amylin activity in vivo in treated test animals, (e.g., provoking marked hyperlactemia followed by hyperglycemia). In addition to having activities characteristic of amylin, certain of the preferred compounds of the invention have also been found to possess more desirable solubility and stability characteristics when compared to human amylin. Examples of these compounds include $^{25}$Pro$^{26}$Val$^{28,29}$Pro-h-amylin, $^{25,28,29}$Pro-h-amylin, and $^{18}$Arg$^{25,28}$Pro-h-amylin.

Other compounds include $^{18}$Arg$^{25,28}$Pro-h-amylin, des-$^1$Lys$^{18}$Arg$^{25,28}$Pro-h-amylin, $^{18}$Arg$^{25,28,29}$Pro-h-amylin, des-$^1$Lys $^{18}$Arg$^{25,28,29}$Pro-h-amylin, $^{25,28,29}$Pro-h-amylin, des-$^1$Lys$^{25,28,29}$Pro-h-amylin, $^{25}$Pro$^{26}$Val$^{28,29}$Pro-h-amylin, $^{23}$Leu$^{25}$Pro$^{26}$Val$^{28,29}$Pro-h-amylin, $^{23}$Leu $^{25}$Pro$^{26}$Val$^{28}$Pro-h-amylin, des-$^1$Lys$^{23}$Leu$^{25}$Pro$^{26}$Val$^{28}$Pro-h-amylin, $^{18}$Arg$^{23}$Leu$^{25}$Pro$^{26}$Val$^{28}$Pro-h-amylin, $^{18}$Arg$^{23}$Leu$^{25,28,29}$Pro-h-amylin, $^{18}$Arg$^{23}$Leu$^{25,28}$Pro-h-amylin, $^{17}$Ile$^{23}$Leu$^{25,28,29}$Pro-h-amylin, $^{17}$Ile$^{25,28,29}$Pro-h-amylin, des-$^1$Lys$^{17}$Ile$^{23}$Leu$^{25,28,29}$Pro-h-amylin, $^{17}$Ile$^{18}$Arg$^{23}$Leu-h-amylin, $^{17}$Ile$^{18}$Arg$^{23}$Leu$^{26}$Val$^{29}$Pro-h-amylin, $^{17}$Ile$^{18}$Arg$^{23}$Leu$^{25}$Pro$^{26}$Val$^{28,29}$Pro-h-amylin, $^{13}$Thr$^{21}$His$^{23}$Leu$^{26}$Ala$^{28}$Leu$^{29}$Pro$^{31}$Asp-h-amylin, $^{13}$Thr$^{21}$His$^{23}$Leu$^{26}$Ala$^{29}$Pro$^{31}$Asp-h-amylin, des-$^1$Lys$^{13}$Thr$^{21}$His$^{23}$Leu$^{26}$Ala$^{28}$Pro$^{31}$Asp-h-amylin, $^{13}$Thr$^{18}$Arg$^{21}$His$^{23}$Leu$^{26}$Ala$^{29}$Pro$^{31}$Asp-h-amylin, $^{31}$Thr$^{18}$Arg$^{21}$His$^{23}$Leu$^{28,29}$Pro$^{31}$Asp-h-amylin, and $^{13}$Thr$^{18}$Arg$^{21}$His$^{23}$Leu$^{25}$Pro$^{31}$Ala$^{28,29}$Pro$^{31}$Asp-h-amylin.

As noted in U.S. Pat. No. 5,677,279, amylin and amylin agonists and analogs may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys (Cl-Z), Fmoc-Lys(Boc), Boc-Glu(Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, methylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and Tboc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−5.degree. C. to 0.degree. C., 1 hour). The peptide may be extracted from the resin with alternating water and acetic acid, and the filtrates lyophilized. The Fmoc-peptide resins may be cleaved according to standard methods (Introduction to Cleavage Techniques, Applied Biosystems, Inc., 1990, pp. 6-12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/$CH_3$ CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen, et al., The Pico Tag Method: A Manual of Advanced Techniques for Amino Acid Analysis, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Peptide compounds useful in the invention may also be prepared using recombinant DNA techniques, using methods known in the art. See, e.g., Sambrook et al., Molecular Cloning: A Laboratory Manual, 2d Ed., Cold Spring Harbor (1989). Non-peptide compounds useful in the present invention may be isolated from appropriate naturally occurring sources and/or prepared by art-recognized synthetic methods.

Amylin agonists and amylin analogs or amylin agonist analogs are recognized as referring to compounds which, by directly or indirectly interacting or binding with one or more receptors, mimics an action of amylin. Such interactions or binding events include those that would alleviate one or more molecular or biological events that lead to the undesirable effects and symptoms of pancreatitis. Useful amylin agonist analogs include those identified in an International Application, WPI Acc. No. 93-182488/22, entitled "New Amylin Agonist Peptides Used for Treatment and Prevention of Hypoglycemia and Diabetes Mellitus," the contents of which is also hereby incorporated by reference.

Activity as amylin agonists and/or analogs can be confirmed and quantified by performing various screening assays, including the nucleus accumbens receptor binding assay, followed by the soleus muscle assay, a gastric emptying assay, or by the ability to induce hypocalcemia or reduce postprandial hyperglycemia in mammals.

The receptor binding assay, a competition assay that measures the ability of compounds to bind specifically to membrane-bound amylin receptors, is described in U.S. Pat. Nos. 5,264,372 and 5,686,411, the disclosures of which are incorporated herein by reference. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand, are analyzed by computer using analyses by nonlinear regression to a 4-parameter logistic equation (Inplot program; GraphPAD Software, San Diego, Calif.) or the ALLFIT program of DeLean et al. (ALLFIT, Version 2.7 (NIH, Bethesda, Md. 20892)). Munson and Rodbard, Anal. Biochem. 107:220-239 (1980).

Assays of biological activity of amylin agonists/analogs in the soleus muscle may be performed using previously described methods (Leighton, B. and Cooper, Nature, 335: 632-635 (1988); Cooper, et al., Proc. Natl. Acad. Sci. USA 85:7763-7766 (1988)), in which amylin agonist activity may be assessed by measuring the inhibition of insulin-stimulated glycogen synthesis. In brief, an exemplary method includes soleus muscle strips prepared from 12-h fasted male Wistar rats. The tendons of the muscles are ligated before attachment to stainless steel clips. Muscle strips are pre-incubated in Erlenmeyer flasks containing 3.5 ml Krebs-Ringer bicarbonate buffer, 7 mM N-2-hydroxyethyl-peperazine-N'-2-ethanesulphonic acid, pH 7.4, and 5.5 mM pyruvate. Flasks are sealed and gassed continuously with $O_2$ and $CO_2$ in the ratio 19:1 (v/v). After pre-incubation of muscles in this medium for 30 min at 37° C. in an oscillating water bath, the muscles strips are transferred to similar vials containing identical medium (except pyruvate) with added [U-$^{14}$C] glucose (0.5 μCi/ml) and insulin (100 μU/ml). The flasks are sealed and re-gassed for an initial 15 min in a 1-h incubation. At the end of the incubation period, muscles are blotted and rapidly frozen in liquid $N_2$. The concentration of lactate in the incubation medium can be determined spectrophotometrically and [U-$^{14}$C]glucose incorporation in glycogen measured.

Methods of measuring the rate of gastric emptying are disclosed in, for example, Young et al. In a phenol red method, conscious rats receive by gavage an acoloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage.

Preferably, amylin agonist compounds exhibit activity in the receptor binding assay on the order of less than about 1 to 5 nM, preferably less than about 1 nM and more preferably less than about 50 pM. In the soleus muscle assay, preferred amylin agonist compounds show $EC_{50}$ values on the order of less than about 1 to 10 micromolar. In the gastric emptying assays, preferred agonist compounds show $ED_{50}$ values on the order of less than 100 μg/rat.

In certain embodiments, the invention comprises the use of other agents known for use in the treatment of pancreatitis, including, but not limited to, an analgesic for pain relief agent. Non-limiting examples of analgesics include narcotics like the naturally occurring opium alkaloids as well as semi-synthetic and synthetic derivatives, examples of which include morphine, pentazocine, hydromorphone, oxymorphone, levorphanol, methadone, meperidine, anileridine, alphaprodine, fentanol, codeine, oxycodone and hydrocordone.

In other embodiment of the invention, the treatment of pancreatitis comprises the administration of an effective amount of an amylin or amylin agonist. The term "effective amount" refers to an amount effective to reduce, ameliorate, inhibit, or eliminate one or more molecular, biological, or clinical effects associated with pancreatitis, whether acute or chronic.

Amylin's observed effects on reducing pancreatic enzyme and gastric acid secretion are rapid, with the onset being several minutes. The therapeutic effect of these actions is important in the prevention of damage (hemorrhage and necrosis) to pancreatic acinar cells and the prevention of pancreatic edema. The therapeutic effect of amylin is also important in preventing the inflammatory response of the pancreas, which results in the appearance of pancreatic exudate with toxins and pancreatic enzymes in retroperitoneum as well as the presence of pancreatic toxins and enzymes in systemic circulation. By preventing this cascade, the pain associated with pancreatitis may be lowered.

Use of an amylin or an agonist/analog thereof in the treatment of pancreatitis according to the invention has the unexpected benefit of simultaneously reducing pancreatic enzyme levels associated with the disease and relieving the pain associated with the disease. This is due to the presence of the pancreatitis alleviating activity being simultaneously present with the analgesic activity of amylin, which is described in U.S. Pat. No. 5,677,279, issued Oct. 14, 1997.

Formulations and Administration

As a related aspect of the invention, pharmaceutical compositions comprising a therapeutically effective amount of an amylin, an amylin agonist and/or an amylin analog as described herein are provided and may be used in the practice of the invention. The compositions may also comprise acceptable salts or pro-drug forms of the amylin, amylin agonist, and/or amylin analog. The amylins, agonists and analogs thereof, of the invention, may form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Other exemplary formulations for an amylin and amylin agonist/analog can be found in U.S. Pat. No. 6,410,511 and U.S. patent application Ser. No. 10/159,779, filed May 31, 2002, which are incorporated herein by reference.

In general, amylin, amylin agonists/analogs may be formulated into a stable, safe pharmaceutical composition for administration to a patient. Pharmaceutical formulations contemplated for use in the methods of the invention may comprise approximately 0.01 to 1.0% (w/v), preferably 0.05 to 1.0%, of an amylin, amylin agonist, or amylin antagonist, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

In a particular embodiment of the present invention, a pharmaceutical formulation of the present invention may contain a range of concentrations of amylin or amylin agonist/analog, e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in this embodiment. A sufficient amount of water for injection may be used to obtain the desired concentration of solution.

Additional tonicifying agents such as sodium chloride, as well as other known excipients, may also be present, if desired. It is preferred, however, if such excipients maintain the overall tonicity of the amylin or amylin agonist/analog. An excipient may be included in the presently described formulations at various concentrations. For example, an excipient may be included in the concentration range from about 0.02% to about 20% w/w, preferably between about 0.02% and 0.5% w/w, about 0.02% to about 10% w/w, or about 1% to about 20% w/w. In addition, similar to the present formulations themselves, an excipient may be included in solid (including powdered), liquid, semi-solid or gel form.

The pharmaceutical formulations may be composed in various forms, e.g., solid, liquid, semisolid or liquid. The term "solid," as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the present peptide formulations, for example, water or an aqueous/organic solvent mixture or suspension.

The stability of a peptide formulation of the present invention is enhanced by maintaining the pH of the formulation in the range of about 3.0 to about 7.0 when in liquid form. Preferably, the pH of the formulation is maintained in the range of about 3.5 to 5.0, or about 3.5 to 6.5, most preferably from about 3.7 to 4.3, or about 3.8 to 4.2. A frequently preferred pH may be about 4.0. While not seeking to be bound by this theory, it is presently understood that where the pH of the pharmaceutical formulation exceeds 5.5, chemical degradation of the peptide may be accelerated such that the shelf life is less than about two years.

The buffer used in the practice of the present invention is an acetate buffer (preferably at a final formulation concentration of from about 1-5 to about 60 mM), phosphate buffer (preferably at a final formulation concentration of from about 1-5 to about to about 30 mM) or glutamate buffer (preferably at a final formulation concentration of from about 1-5 to about to about 60 mM). The most preferred buffer is acetate (preferably at a final formulation concentration of from about 5 to about 30 mM).

A stabilizer may be included in the present formulation but, and importantly, is not necessarily needed. If included, however, a stabilizer useful in the practice of the present invention is a carbohydrate or a polyhydric alcohol. A suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. For patients who have trouble regulating their blood glucose levels, such as diabetics, suitable carbohydrates include: galactose, arabinose, lactose or any other carbohydrate which does not have an adverse affect on blood glucose levels, i.e., the carbohydrate is not metabolized to form unacceptably large concentrations of glucose in the blood. Such carbohydrates are well known in the art as suitable for diabetics. Sucrose and fructose are suitable for use with amylin, amylin agonist/analog in non-diabetic patients.

Preferably, if a stabilizer is included, the amylin, amylin agonist/analog is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Mannitol is the preferred polyhydric alcohol. Another useful feature of the lyophilized formulations of the present invention is the maintenance of the tonicity of the lyophilized formulations described herein with the same formulation component that serves to maintain their stability. Mannitol is the preferred polyhydric alcohol used for this purpose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), the preferred range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

A detailed description of each preservative is set forth in "Remington's Pharmaceutical Sciences" as well as *Pharmaceutical Dosage Forms: Parenteral Medications*, Vol. 1, 1992, Avis et al.

Pramlintide (human $^{25,28,29}$Pro-amylin) does not have a tendency to adsorb onto the glass in a glass container when in a liquid form, therefore, a surfactant is not required to further stabilize the pharmaceutical formulation. However, with regard to amylin and amylin agonist/analog that do have such a tendency when in liquid form, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the peptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl) dimethylammonio] 1-propanesulfonate), Brij® (e.g., Brij 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations are preferably isotonic or substantially isotonic.

The preferred vehicle for parenteral products is water. Water of suitable quality for parenteral administration can be prepared either by distillation or by reverse osmosis. Water for injection is the preferred aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation of the present invention.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type I-33) or its equivalent (Wheaton Glass Co.). Other vendors of similar borosilicate glass vials and cartridges acceptable for manufacture include Kimbel Glass Co., West Co., Bünder Glas GMBH and Form a Vitrum. The biological and chemical properties of amylin may be stabilized by formulation and lyophilization in a Wheaton Type I-33 borosilicate serum vial to a final concentration of 0.1 mg/ml and 10 mg/ml of amylin in the presence of 5% mannitol, and 0.02% Tween 80.

In order to permit introduction of a needle from a hypodermic syringe into a multiple-dose vial and provide for resealing as soon as the needle is withdrawn, the open end of each vial is preferably sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. These stoppers are compatible with the peptide as well as the other components of the formulation. The inventors have also discovered that these stoppers pass the stopper integrity test when tested using patient use patterns, e.g., the stopper can withstand at least about 100 injections. Alternatively, the peptide can be lyophilized in to vials, syringes or cartridges for subsequent reconstitution. Liquid formulations of the present invention can be filled into one or two chambered cartridges, or one or two chamber syringes.

Each of the components of the pharmaceutical formulation described above is known in the art and is described in *Pharmaceutical Dosage Forms: Parenteral Medications*, Vol. 1, 2nd ed., Avis et al. Ed., Mercel Dekker, New York, N.Y. 1992, which is incorporated by reference in its entirety herein.

The manufacturing process for the above liquid formulations generally involves compounding, sterile filtration and filling steps. The compounding procedure involves dissolution of ingredients in a specific order (preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), exposure to a radiation source, and aseptic handling. Filtration is the preferred method of sterilization for liquid formulations of the present invention. The sterile filtration involves filtration through 0.45 μm and 0.22 μm (1 or 2) which may be connected in series. After filtration, the solution is filled into appropriate vials or containers.

The liquid pharmaceutical formulations of the present invention can be for parenteral administration. Suitable routes of administration include intramuscular, intravenous, subcutaneous, intradermal, intraarticular, intrathecal and the like. Mucosal delivery is also contemplated. These routes include, but are not limited to, oral, nasal, sublingual, pulmonary and buccal routes which may include administration of the peptide in liquid, semi-solid or solid form. In general, administration via these routes requires substantially more peptide to obtain the desired biological effects due to decreased bioavailability compared to parenteral delivery. In addition, parenteral controlled release delivery can be achieved by forming polymeric microcapsules, matrices, solutions, implants and devices and administering them orally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842.

As will be recognized by those in the field, an effective amount of the therapeutic agent will vary with many factors including the age and weight of the patient, the patient's physical condition, the condition to be treated, and other factors.

However, exemplary amounts of the compound may be from a lower limit of about 1 μg, 5 μg, 10 μg, 50 μg to 100 μg to an upper limit of about 100 μg, 500 μg, 1 mg, 5 mg, 10 mg, or 50 mg of the amylin or amylin agonist/analog per day, administered in a single, divided or continuous dose. For example, an effective single, divided or continuous doses of the compounds of the invention, including $^{25,28,29}$Pro-h-amylin, $^{18}$Arg$^{25,28,29}$Pro-h-amylin, and $^{18}$Arg$^{25,28}$Pro-h-amylin, may be in the range of 0.01 or 0.03 mg to about 5 mg/day, about 0.01 or 0.5 mg to 2 mg/day, or about 0.01 or 0.1 mg to 1 mg/day, for a 70 kg patient, administered in a single, divided or continuous dose.

Also contemplated are other dose ranges such as 0.1 μg to 1 mg of the compound per dose. The doses per day may be delivered in discrete unit doses, or provided continuously in a 24 hour period or any portion of that the 24 hours. The number of doses per day may be from 1 to about 4 per day, although it could be more. Continuous delivery can be in the form of continuous infusions. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 μg to about 8 mg per day, whereas total dose/delivery of the pharmaceutical composition given s.c may be about 6 μg to about 6 mg per day.

As noted previously, the compositions of the invention may be administered alone or in combination with one or more additional compounds that are used to treat pancreatitis and/or analgesics (i.e., pain relievers). Compounds that may be used in the treatment of pancreatitis may include pancreatic enzymes, vitamins and minerals, and antioxidants. Such combinations may be utilized either by combining the components into a single composition for administration or by administering the components separately as part of one therapeutic protocol. A suitable administration format may be routinely determined by a skilled medical practitioner for each individual patient.

Administration of the compositions of the invention may also be in combination with a regimen used in the treatment of pancreatitis. For example, the regimen may include a dietary change to a low-fat diet, a high carbohydrate diet, and/or avoidance of alcohol. The regimen could include parenteral administration of nutrients or by enteral jejunal feeding. In certain cases, food is avoided for a few days. The treatment for pancreatitis may also include surgery to the pancreas or the ducts found therein.

Administration should begin at the first sign (or symptom) of pancreatitis or as soon as practicable after diagnosis thereof. Administration may be by injection or infusion, preferably intravenous, subcutaneous or intramuscular. Orally active compounds may be taken orally, however dosages should be increased 5-10 fold. Dosages may of course be repeated as deemed necessary by the skilled practitioner.

It should be noted, however, that the foregoing ranges are only suggestive, as the number of variables in regard to an individual treatment regime is large, and considerable excursions from these recommended values are expected and may be routinely made by those skilled in the art as deemed necessary. Effective amounts or doses of the compounds of the invention for treating pancreatitis can be determined using recognized in vitro systems or data from clinical trials.

Having now generally described the invention, the same will be more readily understood through reference to the following examples that are provided by way of illustration, and are not intended to be limiting of the present invention, unless specified.

EXAMPLE I

Effect of Amylin on Caerulein-Induced Pancreatitis

Figure 1:
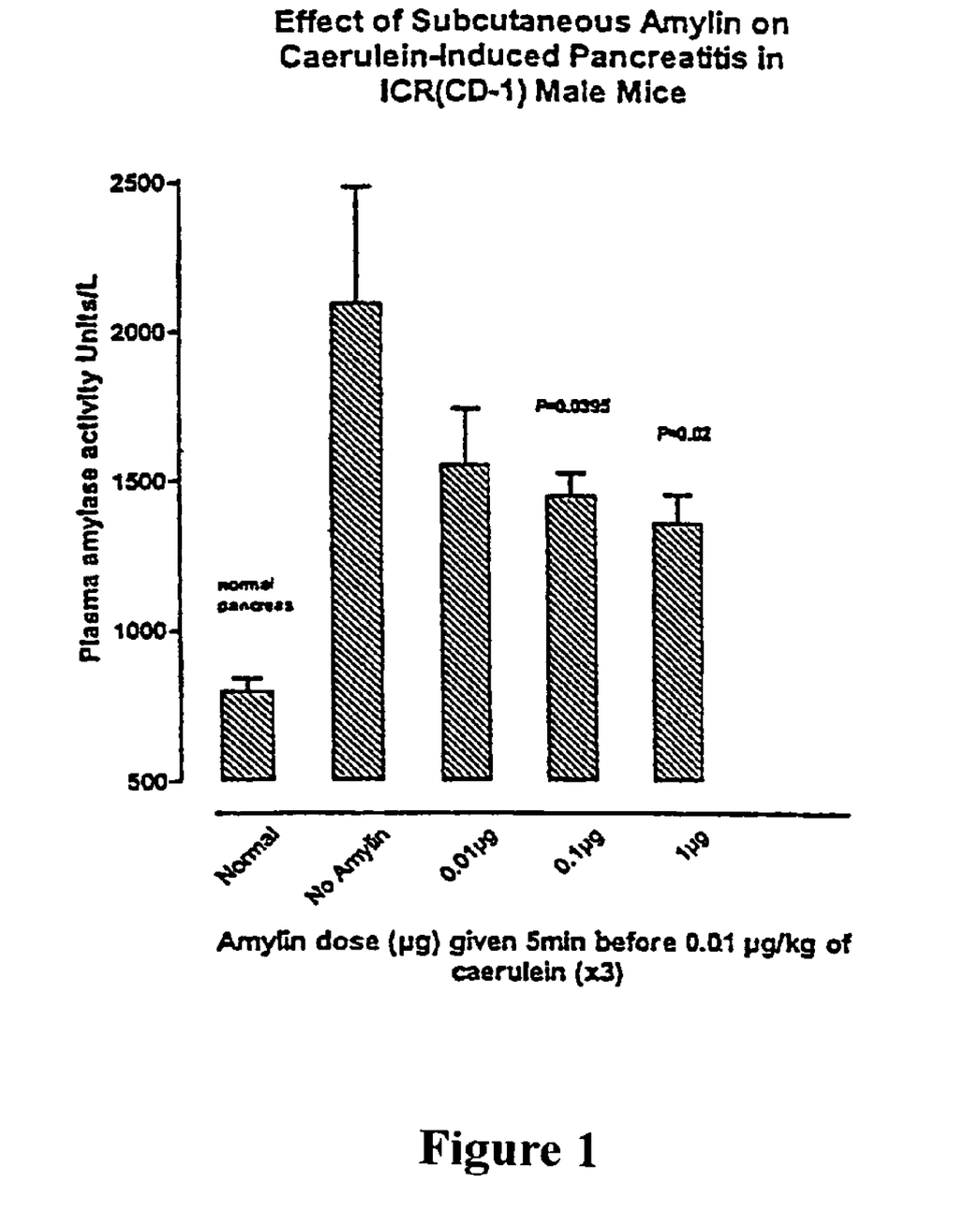
FIG. 1 shows the effect of subcutaneous amylin on caerulein-induced pancreatitis in ICR(CD-1) male mice.
Figure 2A:
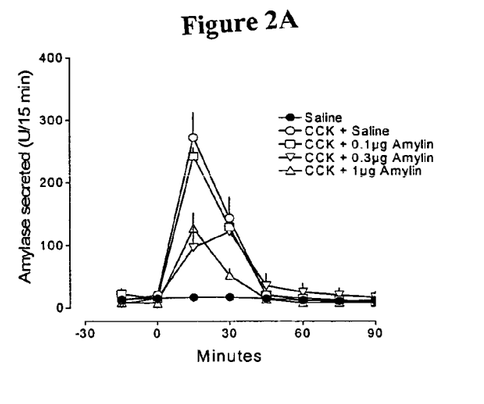
FIGS. 2A-2D show the effects of amylin on the secretion of pancreatic amylase and pancreatic lipase on CCK-8 stimulated pancreatic enzymes.
Figure 2B:
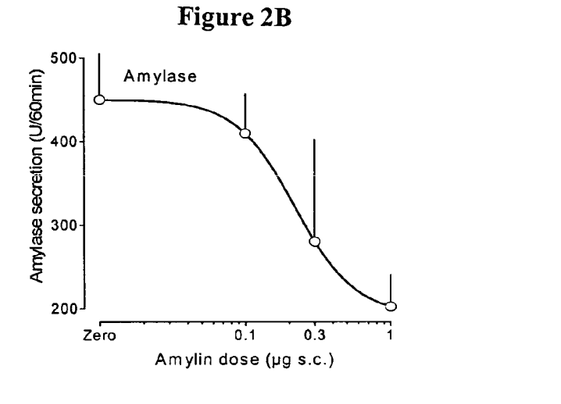
Figure 2C:
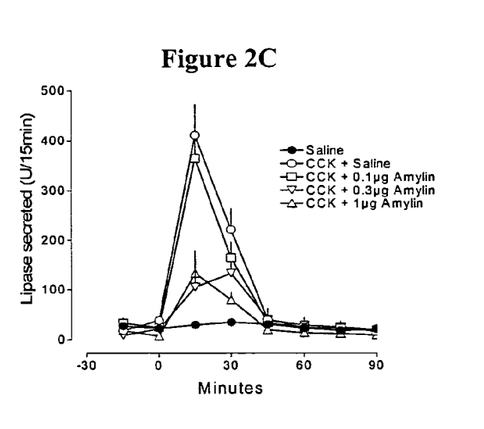
Figure 2D:
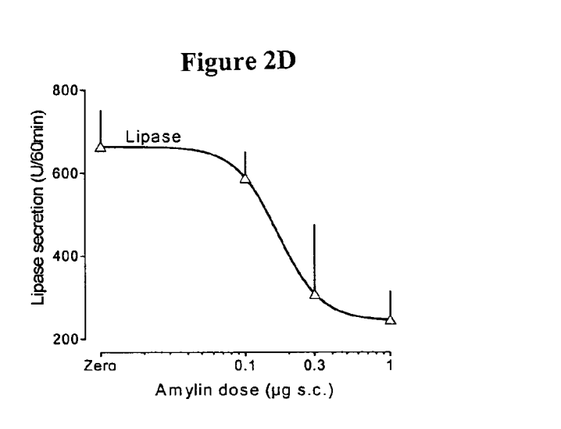

Male ICR mice, weighing approximately 20 g, were fasted overnight and throughout the experiment, but were allowed access to water ad libitum. At t=−5 min, mice were injected with saline (n=8) for normal group, saline (n=5) for no amylin group, 0.01 µg amylin (n=7), 0.1 µg amylin (n=5), or 1 µg amylin (n=8) (AC128, Amylin Pharmaceuticals, Inc.). At t=0, 0.01 µg/kg of caerulein in all but the normal group of mice. The dosing regimen for caerulein was repeated 3 times at 2 hour intervals. At t=9 hours, i.e., 9 hours after the first caerulein injection, the mice were bleed (orbital sinus) and the plasma assayed for amylase (Amylase 3 assay kit, Sigma Diagnostics Catalog #577-3, Sigma Diagnostics, St. Louis, Mo., USA). Results are shown in FIG. 1. Amylin, at levels as low as 0.01 µg, was sufficient to effectively reduce the elevated levels of plasma amylase produced by caerulein.

EXAMPLE II

Inhibition of CCK-8 Stimulated Lipase and Amylase Secretion in Rat Pancreas

Rats, weight 334-399 g after overnight fasting, were anesthetized with 5% halothane, maintained at 2% during surgery and 1% thereafter. Tracheotomy and cannulation of the right femoral artery were performed and body temperature was controlled with a thermoregulator (Model 73A, YSI, Yellow Springs, Ohio, USA) that switched a heated operating table. The femoral arterial line, used for blood sampling, was perfused with heparinized saline (2 u/ml) and connected to a pressure transducer for blood pressure recording (Spectramed P23XL transducer, Model 13-4615-58 amplifier, Gould, Cleveland, Ohio, USA). Through a midline incision two polyethylene cannulae were inserted into the common bile-pancreatic duct at a point about 0.5 cm above where the duct enters the pancreas. The first cannula was inserted up toward the liver to collect bile. The other end of this cannula was placed into the duodenum through a small incision in the duodenum. Thus, bile flowed directly from the liver to the small intestine, being shunted away from the pancreas completely.

A second polyethylene cannula was inserted into the common bile-pancreatic duct near the first but in the opposite direction to collect pancreatic juice. The other end of the pancreatic duct was tied off with a suture just at the point where it enters the duodenum, forcing any pancreatic juice produced to flow through the second cannula for collection. Pancreatic juice was collected every 15 min from −30 to 90 min. Subcutaneous injections of saline, rat amylin(AR905-80) or cholecystokinin octapeptide (CCK-8) (Peninsula #034280 and #441021), or combination of both were performed at time 0 min. The volume of juice was measured and aliquots taken for enzymes determination. Amylase and lipase, which are secreted in pancreatic juice in an active form, were tested using diagnostic kits (Lipase-PS assay kit, Sigma Diagnostics Catalog #805-A and Amylase 3 assay kit, Sigma Diagnostics Catalog #577-3, Sigma Diagnostics, St. Louis, Mo., USA). To perform both assays, pancreatic juice was diluted with saline in proportion 1:2000. Activity of enzymes was expressed in units per 15 min (activity in pancreatic juice collected every 15 min).

There were 7 treatment groups all injected at time 0 min: control saline (n=5), amylin 1, 10 µg (n=5, 5*), CCK-8 1 µg (n=6) or CC-8 1 µg in combination with rat amylin (0.1, 0.3, 1, 10 µg; n=6, 7, 6, 5 respectively).

Results demonstrate that amylin dose-dependently inhibits secretion of cholecystokinin stimulated pancreatic lipase by up to 57.3% and pancreatic amylase activity by up to 67.9%. The $ED_{50}$'s for amylin suppression of pancreatic amylase and lipase activity were 129 pmol/kg±0.09 log units for both enzymes. The $ED_{50}$'s for amylin suppression of CCK-8 stimulated pancreatic amylase and lipase activity were 123 pmol/kg±0.09 log units for both. From rat amylin kinetic studies, it was predicted that this dose can elevate plasma amylin concentrations to within the reported physiological range in fed animals.

TABLE 1

Effects of amylin on pancreatic flow, pancreatic amylase and pancreatic lipase activity with and without CCK-8 stimulation.

| Injections | n | Pancreatic flow µl/45 min | % from CCK-8 stimulated | Amylase U/45 min | % from CCK-8 stimulated | Lipase U/45 min | % from CCK-8 stimulated |
|---|---|---|---|---|---|---|---|
| Saline | 5 | 23 ± 4 | | 49.78 ± 16.90 | | 96.03 ± 25.04 | |
| Amylin 1 µg | 5 | 30 ± 6 | | 80.21 ± 35.71 | | 149.51 ± 86.79 | |
| Amylin 10 µg | 5 | 13 ± 4 | | 61.95 ± 24.51 | | 64.67 ± 21.59 | |
| CCK-8 1 µg | 6 | 99 ± 13 | | 459.76 ± 52.49 | | 723.56 ± 100.56 | |
| CCK-8 and Amylin 0.1 µg | 6 | 78 ± 8 | 21.21 | 340.98 ± 40.91 | 25.83 | 472.82 ± 58.67 | 34.65 |
| CCK-8 and Amylin 0.3 µg | 7 | 67 ± 6 | 32.32 | 271.73 ± 48.38 | 40.90 | 309.30 ± 74.31 | 57.25 |
| CCK-8 and Amylin 1.0 µg | 6 | 58 ± 12 | 41.41 | 193.93 ± 34.40 | 57.32 | 232.41 ± 58.01 | 67.87 |
| CCK-8 and Amylin 10.0 µg | 5 | 90 ± 13 | 9.09 | 353.68 ± 78.85 | 23.07 | 370.65 ± 85.67 | 48.77 |

EXAMPLE III

Exemplary Methods of Making and Assaying the Compounds

Example 1

Preparation of $^{28}$Pro-human-Amylin

Solid phase synthesis of this analogue of human ("h-") amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved, the resin and side chain protecting groups were cleaved with liquid hydrofluoric acid ("HF") in the presence of dimethylsulfide and anisole. The $^{28}$Pro-h-amylin was purified by preparative HPLC. The peptide was found to be homogeneous by analytical HPLC and capillary electrophoresis and the structure confirmed by amino acid analysis and sequence analysis. The product gave the desired mass ion. FAB mass spec: (M+1)/e=3914.

Example 2

Receptor Binding Assay

Evaluation of the binding of compounds of the invention to amylin receptors was carried out as follows. $^{125}$I-rat amylin (Bolton-Hunter labeled at the N-terminal lysine) was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200-250) grams were sacrificed by decapitation. Brains were removed to cold phosphate-buffered saline (PBS). From the ventral surface, cuts were made rostral to the hypothalamus, bounded laterally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000×g. The final membrane pellet was resuspended in 20 mM HEPES buffer containing 0.2 mM phenylmethylsulfonyl fluoride (PMSF).

To measure $^{125}$I-amylin binding, membranes from 4 mg original wet weight of tissue were incubated with $^{125}$I-amylin at 12-16 pM in 20 mM HEPES buffer containing 0.5 mg/ml bacitracin, 0.5 mg/ml bovine serum albumin, and 0.2 mM PMSF. Solutions were incubated for 60 minutes at 23° C. Incubations were terminated by filtration through GF/B glass fiber filters (Whatman Inc., Clifton, N.J.) which had been presoaked for 4 hours in 0.3% poylethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%. Competition curves were generated by measuring binding in the presence of $10^{-12}$ to $10^{-6}$ M unlabeled test compound and were analyzed by nonlinear regression using a 4-parameter logistic equation (Inplot program; GraphPAD Software, San Diego).

In this assay, purified human amylin binds to its receptor at a measured $IC_{50}$ of about 50 pM. Results for test compounds of the invention are set forth in Table I, showing that each of the compounds has significant receptor binding activity.

Example 3

Soleus Muscle Assay

Evaluation of the amylin agonist activity of compounds of the invention was carried out using the soleus muscle assay as follows. Male Harlan Sprague-Dawley rats of approximately 200 g mass were used in order to maintain mass of the split soleus muscle less than 40 mg. The animals were fasted for 4 hours prior to sacrifice by decapitation. The skin was stripped from the lower limb which was then pinned out on corkboard. The *tendo achilles* was cut just above *os calcis* and *m. gastrocnemius* reflected out from the posterior aspect of the tibia. *M. soleus*, a small 15-20 mm long, 0.5 mm thick flat muscle on the bone surface of *m. gastrocnemius* was then stripped clear and the perimysium cleaned off using fine scissors and forceps. *M. soleus* was then split into equal parts using a blade passed antero-posteriorly through the belly of the muscle to obtain a total of 4 muscle strips from each animal. After dissecting the muscle from the animal, it was kept for a short period in physiological saline. It was not necessary that the muscle be held under tension as this had no demonstrable effects on radioglucose incorporation into glycogen.

Muscles were added to 50 mL Erlenmeyer flasks containing 10 mL of a pregassed Krebs-Ringer bicarbonate buffer containing (each liter) NaCl 118.5 mmol (6.93 g), KCl 5.94 mmol (443 mg), $CaCl_2$ 2.54 mmol (282 mg), $MgSO_4$ 1.19 mmol (143 mg), $KH_2PO_4$ 1.19 mmol (162 mg), $NaHCO_3$ 25 mmol (2.1 g), 5.5 mmol glucose (1 g) and recombinant human insulin (Humulin-R, Eli Lilly, Ind.) and the test compound, as detailed below. pH at 37° C. was verified as being between 7.1 and 7.4. Muscles were assigned to different flasks so that the 4 muscle pieces from each animal were evenly distributed among the different assay conditions. The incubation media were gassed by gently blowing carbogen (95% $O_2$, 5% $CO_2$) over the surface while being continuously agitated at 37° C. in an oscillating water bath. After a half-hour "preincubation" period, 0.5 μCi of U-$^{14}$C-glucose was added to each flask which was incubated for a further 60 minutes. Each muscle piece was then rapidly removed, blotted and frozen in liquid $N_2$, weighed and stored for subsequent determination of $^{14}$C-glycogen.

$^{14}$C-glycogen determination was performed in a 7 mL scintillation vial. Each frozen muscle specimen was placed in a vial and digested in 1 mL 60% potassium hydroxide at 70° C. for 45 minutes under continuous agitation. Dissolved glycogen was precipitated out onto the vial by the addition of 3 mL absolute ethanol and overnight cooling at −20° C. The supernatant was gently aspirated, the glycogen washed again with ethanol, aspirated and the precipitate dried under vacuum. All ethanol is evaporated to avoid quenching during scintillation counting. The remaining glycogen was redissolved in 1 mL water and 4 mL scintillation fluid and counted for $^{14}$C.

The rate of glucose incorporation into glycogen (expressed in μmol/g/hr) was obtained from the specific activity of $^{14}$C-glucose in the 5.5 mM glucose of the incubation medium, and the total $^{14}$C counts remaining in the glycogen extracted from each muscle. Dose/response curves were fitted to a 4-parameter logistic model using a least-squares iterative routine (AL-LFIT, v2.7, NIH, Maryland) to derive $EC_{50}$'s. Since $EC_{50}$ is log-normally distributed, it is expressed ± standard error of the logarithm. Pairwise comparisons were performed using t-test based routines of SYSTAT (Wilkinson, "SYSTAT: the system for statistics," SYSTAT Inc., Evanston Ill. (1989)).

Dose response curves were generated with muscles added to media containing 7.1 nM (1000 μU/mL) insulin and each test compound added at final (nominal) concentrations of 0, 1, 3, 10, 30, 100, 300 and 1000 nM. Each assay also contained internal positive controls consisting of a single batch of archived rat amylin, lyophilized and stored at −70° C.

Human amylin is a known hyperglycemic peptide, and $EC_{50}$ measurements of amylin preparations in the soleus muscle assay range typically from about 1-10 nM, although some commercial preparations which are less than 90% pure have higher $EC_{50}$'s due to the presence of contaminants that result in a lower measured activity.

All references cited herein, including patents, patent applications, and publications, are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without undue experimentation.

This application is intended to cover any variations, uses, or adaptations of the invention, following in general the principles of the invention, that include such departures from the present disclosure as come within known or customary practice within the art to which the invention pertains and as may be applied to the essential features hereinbefore set forth.

The invention claimed is:

1. A method of treating pancreatitis in a mammalian subject afflicted with pancreatitis comprising
administering to said subject an effective amount of an amylin or an amylin analog, wherein the amylin analog has amylin agonist activity,
wherein the level of enzymatic activity and/or enzymatic secretion in pancreatic cells of said subject is reduced or inhibited.

2. The method of claim 1 wherein said subject is a human.

3. The method of claim 1 wherein said amylin analog is $^{25,28,29}$Pro-h-amylin.

4. The method of claim 1 wherein 0.1 μg to 1 mg of said amylin or said amylin analog is administered to said mammalian subject in a single, divided, or continuous dose.

5. The method of claim 1 wherein about 2 μg to about 8 mg per day of said amylin or said amylin analog is administered to said mammalian subject.

6. The method of claim 1 wherein the amylin or amylin analog is amylin.

7. The method of claim 1 wherein the pancreatitis is acute pancreatitis.

8. The method of claim 1 wherein the pancreatitis is chronic pancreatitis.

9. The method of claim 7 further comprising administering to the subject an agent or regimen used to treat acute pancreatitis.

10. The method of claim 9 wherein the agent is clinically used to treat pancreatitis.

11. The method of claim 9 wherein the agent is a pancreatic enzyme.

12. The method of claim 9 wherein the regime includes a low-fat diet.

13. The method of claim 9 further comprising administering to said subject an analgesic.

* * * * *

```
                         SEQUENCE LISTING

<160> NUMBER OF SEQ ID NOS: 2

<210> SEQ ID NO 1
<211> LENGTH: 37
<212> TYPE: PRT
<213> ORGANISM: Human

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MISC_FEATURE
<222> LOCATION: (1)..(1)
<223> OTHER INFORMATION: X is Lys, Ala, Ser or hydrogen
<220> FEATURE:
<221> NAME/KEY: MISC_FEATURE
<222> LOCATION: (2)..(2)
<223> OTHER INFORMATION: X at position 2 and X at position 7 are
      independently selected amino acid residues having side chains
      which are chemically bonded to each other to form an
      intramolecular linkage
<220> FEATURE:
<221> NAME/KEY: MISC_FEATURE
<222> LOCATION: (7)..(7)
<223> OTHER INFORMATION: X at position 2 and X at position 7 are
      independently selected amino acid residues having side chains
      which are chemically bonded to each other to form an
      intramolecular linkage
<220> FEATURE:
<221> NAME/KEY: MISC_FEATURE
<222> LOCATION: (13)..(13)
<223> OTHER INFORMATION: X is Ala, Ser or Thr
<220> FEATURE:
<221> NAME/KEY: MISC_FEATURE
<222> LOCATION: (17)..(17)
<223> OTHER INFORMATION: X is Val, Leu or Ile
<220> FEATURE:
<221> NAME/KEY: MISC_FEATURE
<222> LOCATION: (18)..(18)
<223> OTHER INFORMATION: X is His or Arg
<220> FEATURE:
<221> NAME/KEY: MISC_FEATURE
<222> LOCATION: (19)..(19)
<223> OTHER INFORMATION: X is Ser or Thr
<220> FEATURE:
<221> NAME/KEY: MISC_FEATURE
<222> LOCATION: (20)..(20)
<223> OTHER INFORMATION: X is Ser, Thr, Gln or Asn
<220> FEATURE:
<221> NAME/KEY: MISC_FEATURE
<222> LOCATION: (21)..(21)
<223> OTHER INFORMATION: X is Asn, Gln or His
```

```
<220> FEATURE:
<221> NAME/KEY: MISC_FEATURE
<222> LOCATION: (23)..(23)
<223> OTHER INFORMATION: X is Phe, Leu or Tyr
<220> FEATURE:
<221> NAME/KEY: MISC_FEATURE
<222> LOCATION: (25)..(25)
<223> OTHER INFORMATION: X is Ala or Pro
<220> FEATURE:
<221> NAME/KEY: MISC_FEATURE
<222> LOCATION: (26)..(26)
<223> OTHER INFORMATION: X is Ile, Val, Ala or Leu
<220> FEATURE:
<221> NAME/KEY: MISC_FEATURE
<222> LOCATION: (28)..(28)
<223> OTHER INFORMATION: X is Ser, Pro, Leu, Ile or Thr
<220> FEATURE:
<221> NAME/KEY: MISC_FEATURE
<222> LOCATION: (29)..(29)
<223> OTHER INFORMATION: X is Ser, Pro or Thr
<220> FEATURE:
<221> NAME/KEY: MISC_FEATURE
<222> LOCATION: (31)..(31)
<223> OTHER INFORMATION: X is Asn, Asp, or Gln

<400> SEQUENCE: 2

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
            20                  25                  30

Gly Ser Asn Thr Tyr
            35
```